United States Patent [19]

Johnson

[11] 4,017,975
[45] Apr. 19, 1977

[54] SALIVA EJECTOR AND CHIN HOLDER THEREFOR

[76] Inventor: Wesley Grant Johnson, 1642 Mockinbird Place, Orange, Calif. 92667

[22] Filed: Mar. 22, 1976

[21] Appl. No.: 669,244

[52] U.S. Cl. .................................................. 32/33
[51] Int. Cl.² ......................................... A61C 17/04
[58] Field of Search ......................... 32/33; 128/276

[56] References Cited

UNITED STATES PATENTS

| | | | |
|---|---|---|---|
| 2,777,248 | 1/1957 | Hirsch et al. | 46/95 |
| 3,029,513 | 4/1962 | Fletcher | 32/33 |

Primary Examiner—Robert Peshock
Attorney, Agent, or Firm—Gausewitz, Carr & Rothenberg

[57] ABSTRACT

A saliva ejector is formed with a flattened body having an internal suction passage extending along the bottom and continuous to the top of the body. Suction apertures are provided in both the bottom and the top so that suction relief is provided at the top of the ejector, even though lower apertures are blocked by soft tissue. The body of the ejector is made of two mating plates that are snapped together and clamp over the end of a vacuum tube to be connected to the ejector. The extent of the flattened body above its bottom portion permits it to act as a tongue guard, separating the tongue from the teeth, and facilitates location of the vacuum relief ports. A chin holder, having an integral side opening clamp is readily clamped on the vacuum tube to securely position the ejector within the oral cavity.

35 Claims, 10 Drawing Figures

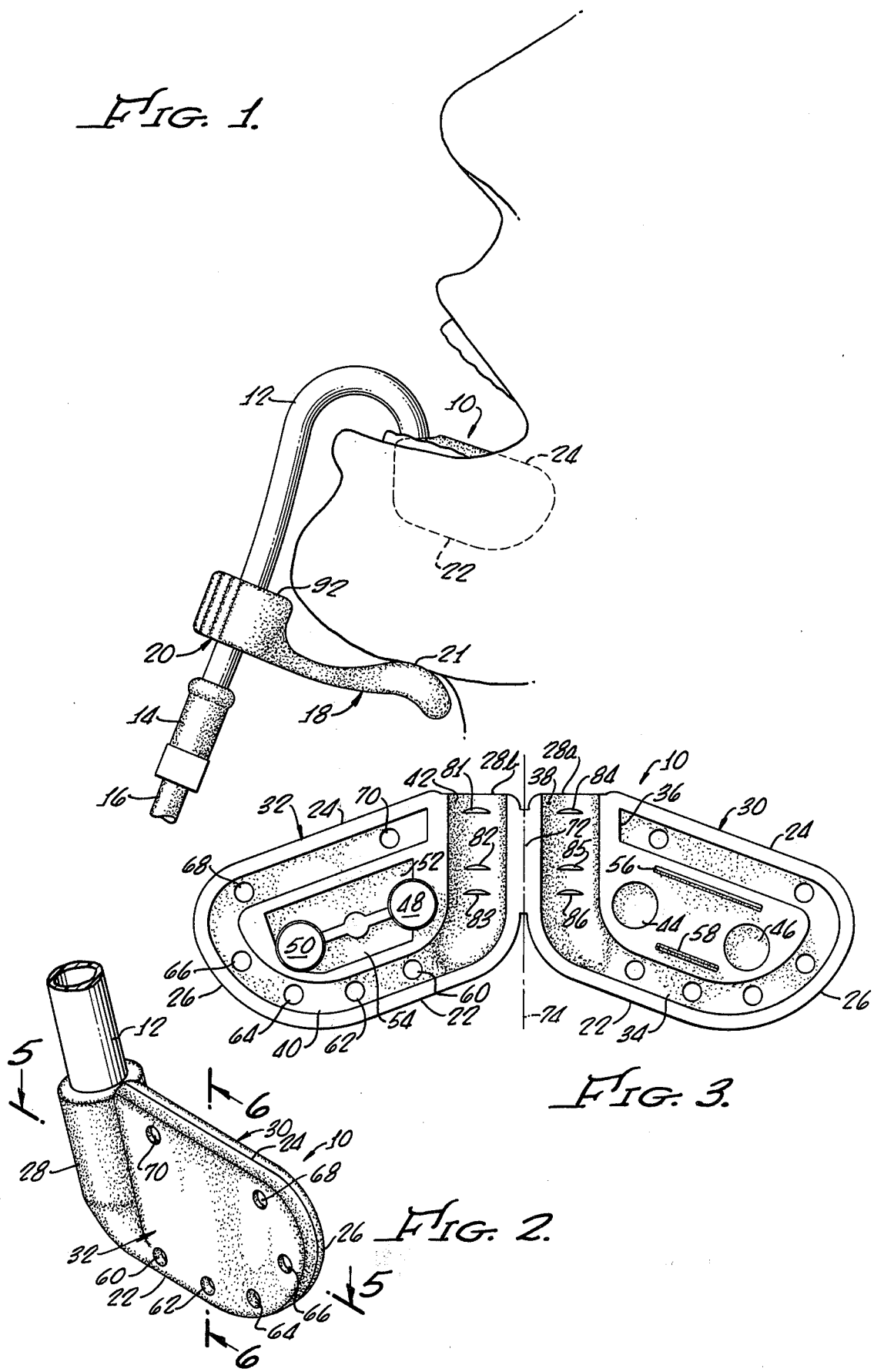

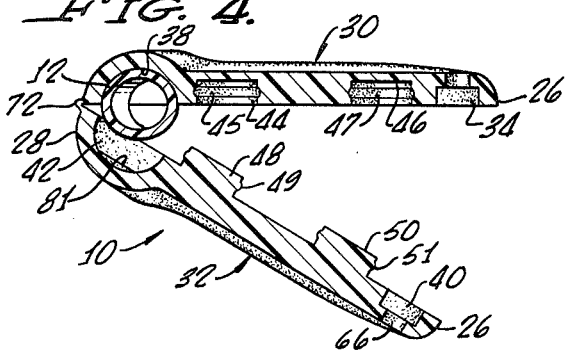
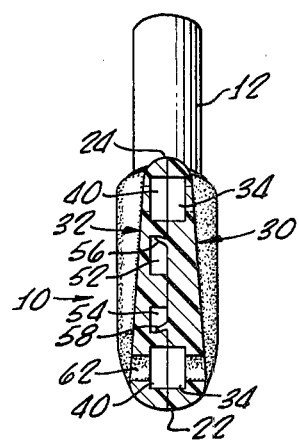
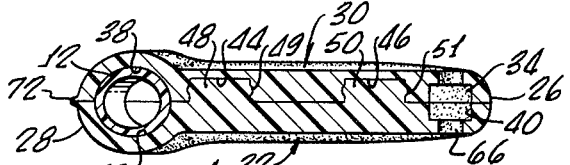
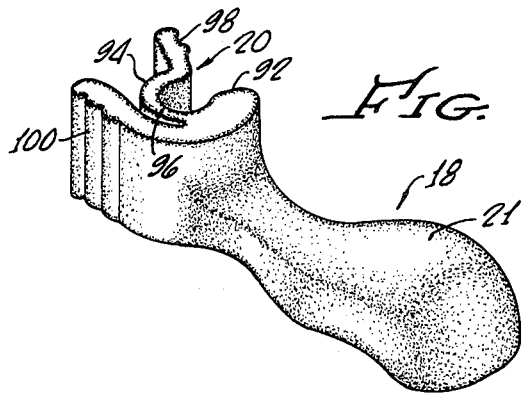
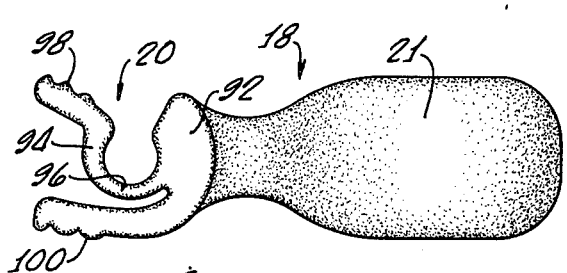
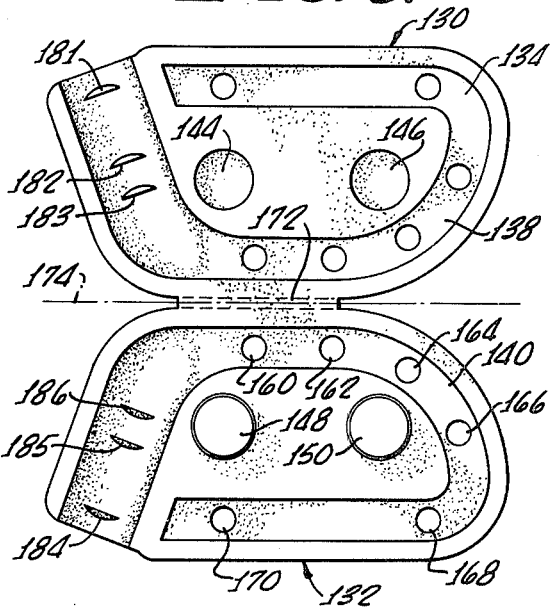
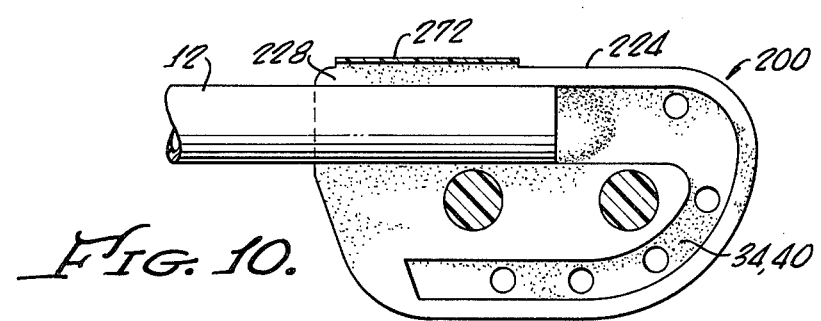

SALIVA EJECTOR AND CHIN HOLDER THEREFOR

BACKGROUND OF THE INVENTION

The present invention relates to saliva ejectors and more particularly concerns an improved saliva ejector capable of acting as a tongue guard. In another of its features, the invention relates to a chin holder, particularly adapted for use with dental appliances, such as saliva ejectors.

Dental saliva ejectors commonly used take a variety of forms and most generally include a vacuum tube upon which is secured an apertured tip that is inserted into the oral cavity so that liquids may be continuously withdrawn while various work is being performed. For certain types of work, it is also necessary to hold the tongue away from the work area and thus devices, such as shown in the U.S. Patents to Nordin U.S. Pat. No. 2,603,870 and White, U.S. Pat. Nos. 2,958,130 and 3,078,578 have been suggested. Such devices are either combined with a saliva ejector or used therewith and may also include a chin holder adjustably mounted upon the vacuum tube of the ejector.

The apparatus of the Nordin patent simply mounts a polished metal plate upon a tubular saliva ejector for use as a tongue guard. In this arrangement, the soft tissue at the bottom of the inside of the mouth may readily be drawn partially into the holes of the saliva ejector, which lies entirely at the bottom of the mouth, and thus block these openings, to disable its operation. Further, the plate is subject to dislodgement from its supporting relation with the saliva ejector and at best is but loosely secured to its support.

The chin holder of the Nordin patent is insertable upon the vacuum tube only from an end of the tube and thus cannot be attached to or detached from the tube after the ejector is in place without disturbing either the tube or the ejector.

The arrangements of White are costly and complex involving multi-part structures movably attached to the vacuum tube and having parts insertable into the mouth for holding the mouth and/or tongue in desired position. Such devices are bulky, unwieldy, expensive and uncomfortable.

The patent to Rogers 3,787,978, illustrates an adjustable chin clamp with a self-locking arrangement. This clamp too, like the arrangement of Nordin, can only be attached to or removed from the vacuum tube by inserting it over one end of the tube.

U.S. Pat. Nos. 1,557,744, 2,830,371, 2,937,445, 3,363,622, 3,631,598, 3,777,756, 3,802,081 and 3,864,831 show some of many other types of saliva ejectors, mirrors, chin holders and tongue guards that have been suggested, but which are subject to problems enumerated above.

Accordingly, it is an object of the present invention to provide an improved saliva ejector which substantially eliminates or minimizes the above-mentioned problems.

SUMMARY OF THE INVENTION

In carrying out principles of the present invention in accordance with a preferred embodiment thereof, a saliva ejector is formed of a flattened body having upper and lower portions, a suction passage being formed in the body and a plurality of apertures communicating with the passage. The body has a height sufficient to extend from the floor of the mouth to the teeth, so that the body may extend along inner sides of the teeth to block contact between the tongue and at least some of the teeth. The height of the body enables a suction passage to extend to the upper portion of the body so that a suction relief port may be provided. In a preferred form the body is made of a pair of plates having mating recesses and grooves to define a suction passage and a vacuum tube receiving opening, the plates being latched together. According to another feature of the invention, a chin holder is formed of a substantially C-shaped body having first and second mutually spaced side legs interconnected by an intermediate leg, at least one of the legs being formed of a resilient material. Handles are formed on the first and second legs, extending in spaced justaposition so that they may be moved relative to each other to force the side legs away from each other and permit the side opening clamp to be attached to, adjusted along and removed from the vacuum tube of the dental appliance without disturbing the appliance or tube.

BRIEF DESCRIPTION OF THE DRAWINGS:

FIG. 1 illustrates a saliva ejector and chin holder embodying principles of the present invention in place upon a patient;

FIG. 2 is an enlarged perspective view of a saliva ejector and part of an attached vacuum tube;

FIG. 3 illustrates the saliva ejector of FIG. 2 before it is engaged upon the vacuum tube;

FIG. 4 is a section through the saliva ejector and tube of FIG. 2 showing the two mating ejector plates in partly closed position;

FIG. 5 is a section taken on lines 5—5 of FIG. 2;

FIG. 6 is a vertical section taken on lines 6—6 of FIG. 2;

FIG. 7 is an enlarged perspective view of the chin holder of FIG. 1;

FIG. 8 is a top plan view of the chin holder of FIG. 7;

FIG. 9 is a view of two plates of a modified form of a saliva ejector, shown in open position; and FIG. 10 is a side view of still another form of saliva ejector shown in position upon a fragment of the end of a vacuum tube.

DETAILED DESCRIPTION

As shown in FIG. 1, a saliva ejector 10 is carried upon the end of a bent saliva ejector tube or vacuum tube 12 which is detachably inserted in a saliva ejector tube holder 14 secured to a vacuum tube line 16 which is connected to a source of vacuum (not shown). A chin holder 18 including a side opening clamp body 10 and an elongated tongue 21, is adjustably mounted upon the vacuum tube 12 so as to firmly engage beneath the chin of a patient. The chin holder is adjusted along the length of tube 12 so as to position and hold the saliva ejector 10 within the oral cavity. Preferably, the chin holder 18 and the bend placed in the tube 12 (which conventionally retains the position in which it is bent) are adjusted to position and hold the ejector 10 with its bottom edge 22 bearing firmly against the floor of the oral cavity, between the tongue and the teeth.

The ejector has a height sufficient to place its upper edge 24 at or about the level of the occlusal surfaces of teeth when the bottom 22 is at the floor of the oral cavity. The latter, of course, is soft enough so that the ejector 10 may be readily adjusted vertically by pressing it downwardly against the floor of the oral cavity with more or less force to position its upper edge 24 at a height sufficient to maintain the tongue separated from the teeth. Thus, the tongue is held in a position where it will not interfere with work on the teeth and, concomitantly, saliva is extracted from the oral cavity.

As can be seen in FIG. 2, the saliva ejector body has a substantially flattened shape, having two long or major dimensions and a minor dimension. The two major dimensions are a vertical dimension as measured between the ejector bottom 22 and top 24 and a horizontal dimension as measured between a forward edge 26 and a rearwardly positioned neck 28. The minor dimension is normal to the plane of the two major dimensions and comprises the relatively small thickness of this narrow flattened body.

The body of the saliva ejector is formed of a pair of substantially congruent and mating plates 30, 32. Plate 30 is formed with a recess 34 extending along the bottom of the plate continuing along the front of the plate and then extending along the top of the plate to a closed end 36. Recess 34 is continuous, following the edges of the plate and terminating at the rear of the plate in an enlarged groove 38 formed in the neck 28a of the plate 30.

Plate 32 has a similar recess 40 extending from a closed end at the top rear edge of the plate forwardly along the edge of the plate, downwardly along the front edge and rearwardly along the bottom edge where it terminates at a groove 42 formed in the neck 28b of plate 32.

Resilient latch means with integral mating parts are provided to securely hold the two plates together. Plate 30 has a pair of substantially circular cross-section wells 44, 46 formed therein for cooperation with projecting pins 48, 50 formed in the plate 32. Wells 44, 46 are formed with peripheral enlarged annuli 45, 47 which cooperate with peripheral enlarged rings 49, 51 on projecting pins 48, 50 so as to securely lock the two plates together when the pins 48, 50 are pressed into the wells 44, 46, as best shown in FIG. 5.

Plate 32 is formed with additional recessed portions 52, 54 which cooperate with projecting ribs 56, 58 on plate 30. Projecting ribs 56, 58 are slightly outwardly divergent and the corresponding walls of the recesses 52, 54 which engage ribs 56, 58 (as best seen in FIG. 6) are slightly convergent inwardly so that when the two plates 30, 32 are pressed together, these ribs and recesses also cooperate to firmly retain the two plates in face to face contiguity and thus maintain the leak free integrity of the vacuum passage formed by the cooperating and mating recesses 34, 40.

Each plate is formed with a plurality of apertures communicating with the vacuum passage, such as indicated at 60, 62, 64, 66, 68 and 70 in plate 32 of FIG. 2. Apertures 60, 62, 64 and 66 may be considered to be the primary saliva aspirating apertures. The relatively great vertical extent or height of the ejector body above its bottom edge 22 enables the apertures, such as apertures 68 and 70, that extend into the portion of the vacuum passage extending along the upper edge of the ejector, to remain clear of the soft tissue of the oral cavity. Thus, these upper apertures are substantially immune to blockage by such soft tissue. Suction relief apertures 68, 70 at the upper edge of the aspirator form relief ports for the vacuum passage.

The grooves 38, 42, which communicate with the passage recesses 34, 40 of the respective plates 30, 32 are enlarged as compared to the passage recesses and each has a substantially semi-circular configuration to collectively define a circular cross-section vacuum tube receiving opening in the neck sections 28a and 28b of the neck 28 of the saliva ejector.

The ejector is preferably molded in a single piece, with the two plates initially formed in a fully opened side by side relation illustrated in FIG. 3. The two plates 30, 32 are molded integrally with one another and are interconnected at the junction between the neck section 28a and 28b by a relatively thin interconnecting section 72 that permits the two plates 30, 32 to pivot with respect to one another about a hinge axis (denoted by a line 74) that extends parallel to the axis of the cylindrical vacuum tube receiving opening defined by the interior of the two neck sections 28a and 28b. If deemed necessary or desirable, molded projections 81, 82, 83, 84, 86, 86 are formed on the interior surfaces of the neck sections 28a and 28b, having sharper corners or edges on their downwardly (as viewed in FIG. 3) facing edges in order to more firmly grasp the surface of the vacuum tube 12 and to better clamp the tube against inadvertent withdrawal from the cylindrical receiving opening.

The plates 30 and 32 are molded of a suitable rigid or semi-rigid plastic with the hinge section 72 being thin enough to allow a hinged pivoting (actually a bending of section 72) of one of the plates relative to the other. The plates can pivot through a full 180° from the position shown in FIG. 3 to that shown in FIG. 5, so that the two plates may be securely latched to each other by the lugs or pins 48, 50 and the ribs 56, 58. The inherent resilience of the plastic of which the ejector body is molded allows the outward divergence of ribs 56, 58 and inward divergence of outer sides of recessed portions 52, 54 to be formed in the molding process while still allowing the parts to be removed from the mold. Conveniently, the ejector is disposable so that it may be used but once and then thrown away. However, it may be sterilized for reuse. When the ejector body is formed of some types of more brittle material, hinge section 72 may be reinforced with an additional and more flexible strip of hinging material (not shown) that may be readily pressure or heat bonded to the hinge section 72. Further, the two plates need not be made integrally with one another but may be made separately and thereafter either hingedly attached, or such hinged attachment may be completely omitted and the two separate plates merely snapped together over the vacuum tube 12. Tube 12 is placed in position within one of the grooves of the plates before the plates are connected to or pivoted toward each other and latched together.

Preferably suction holes are provided in both plates and also in the upper portion so that there will still be unplugged holes on that plate which is away from the mouth tissue. The holes are preferably near but not at the bottom so as to avoid roughness on the bottom of the ejector. The ejector can also be inserted from the side of the mouth adjacent to front teeth to keep the tongue away from the front teeth.

Although recesses and grooves in both plates are shown and preferred, the suction recess and passage may be formed entirely in one plate having an open side that is closed by a cooperating flat inner surface of the adjoining plate.

In order to more firmly and securely position the saliva ejector in the desired location and orientation, there is provided a self-contained and unitary chin holder and side opening clamp for use as described above in connection with the explanation of FIG. 1. The chin holder 18 includes an elongated tongue 21 having a rounded upper edge and extending from an integral connection with one side leg of the side opening clamp 20. The clamp 20 has a body portion including a first side leg 92, a second side leg 94 and an intermediate leg 96 interconnecting the side legs 92, 94 to provide a generally C-shaped clamp body having a part circular opening that faces to the side of the chin holder.

A first handle 98 is connected with and extends laterally outwardly from the free end of one side leg 94. A second handle 100 is connected with the second side leg 92, extending along this leg and along the intermediate leg 96 in spaced relation thereto. The two handles 98, 100 extend in nearly the same direction, toward one side of the clamp body and the tongue 21 extends laterally from the opposite side of the clamp body.

The clamp body, handles and tongue are all integrally formed, preferably by injection molding, of a strong resilient and semi-rigid plastic. The two handles 98, 100 extend in juxtaposition with one another so that they may be readily grasped between the thumb and forefinger and moved toward each other to cause the clamp legs 92, 94 to be moved away from each other to enable attachment to and withdrawal from the vacuum tube 12. Further, the handles may be slightly pressed toward each other to loosen the clamp so that it may be slidably adjusted along the length of the vacuum tube.

The handles extend laterally from a side opposite the side of the chin engaging tongue 21 so that the clamp may be most readily manipulated, with a minimum of interference with the tongue 21, from a position directly in front of the patient most convenient for the operator.

Although the handle 100 is positioned in relatively close proximity to the handle 98, it is connected to the opposite leg 92. Thus, considering a significant part of the bending of the clamp to occur at the intermediate leg 96, the described arrangement of the handle provides a maximum amount of leverage since both of the handles are connected to the extreme opposite ends of the side legs 92, 94 and are so positioned that when they are pressed toward each other, a force is imparted to the ends of the side legs and tends to increase the size of the side opening of the clamp body.

Illustrated in FIG. 9 is a modification of the saliva ejector of FIGS. 1, 2, 3, 4, 5 and 6 in which the two plates 130, 132 are again integrally formed with one another and hingedly interconnected for movement from the completely flat open condition illustrated in FIG. 9 (the condition in which they are molded through 180° to be snapped into and latched to one another with the end of a vacuum tube clamped therebetween. In this embodiment, however, the two plates are interconnected by a hinge section 172 which allows pivotal motion of the plates relative to one another about a hinge line 174 that is parallel to the extent of the lower section of the suction passage recesses 134, 140 that are formed in the plates. The suction passage forming recesses 134, 140, the several suction apertures 160, 162, 164, 166, 168 and 170, grooves 134, 140, tube confining projections 181, 182, 183, 184, 185 and 186 are all identical to the corresponding elements of the embodiment of FIGS. 1 through 6, being designated by corresponding reference numerals having the prefix 1 so that plate 130 of FIG. 9, for example, corresponds to plate 30 of FIG. 3.

The arrangement of FIG. 9 also employs means for latching the two plates together in the form of recesses or wells 144, 146 in plate 130 and projecting lugs or pins 148, 150 in plate 132, the pins being received and resiliently retained within the well, to firmly hold the two plates together. In this arrangement the recesses 52, 54 and ribs 56, 58 of FIG. 3 are omitted so that the inner surface of the body portion of each of the plates within the area defined by the nearly circumscribing vacuum passage is substantially flat for each plate except for the formation of the wells and lugs in the respective plates. It will be readily appreciated that these two parts may be hinged together in other areas, or as previously mentioned, may not even be hinged, but merely made separately and simply pressed together with an end of a vacuum tube clamped therebetween.

Illustrated in FIG. 10 is still another embodiment in which the two plates are hinged together by a hinge section 272, at the rear portion of the upper edge of the plates. In this embodiment, the ejector neck 228 is also formed at the rear of the upper portion of the ejector so that the vacuum tube receiving opening defined by the grooves in each plate extends substantially horizontally (in the normal position of use of the ejector) and rearwardly, parallel to the upper edge 224 of ejector 200.

The arrangement illustrated in FIG. 10 allows the ejector to be employed with less bending of the vacuum tube 12 and may be advantageous for certain desired positioning of the ejector. Except for the rearrangement of the hinged interconnecting section of the plate and the position of the vacuum tube receiving groove and suction passage 34, 40 (together with suction apertures) the ejector is identical to those previously described. In this arrangement, it will be noted that the passage is, in effect, turned upside down with its closed end at the rear of the bottom of the ejector body and with its open end terminating at the upper portion of the ejector body for communication with the vacuum tube receiving opening of the ejector.

There has been described a unitary and firmly supported saliva ejector shaped to act as a tongue guard or restraint and is configured for ease of manufacture and simplicity of installation and use. The ejector may be employed with an improved chin holder having a side opening clamp to enable firm positioning of the ejector.

The foregoing detailed description is to be clearly understood as given by way of illustration and example only, the spirit and scope of this invention being limited solely by the appended claims.

What is claimed is:

1. A combined saliva ejector and tongue restraint adapted to be placed within the oral cavity between the tongue and teeth, said ejector comprising,
   a flattened body having upper and lower portions, said body including,
   first and second plates in face to face contiguity, at least one of said plates being formed with a recess extending along a surface thereof that faces the other of said plates to define a suction passage between said plates in at least said lower portion,
   and means for holding said plates in said face to face contiguity,
   said body being formed with a plurality of apertures communicating with said passage, said body having a height sufficient to extend from the floor of the mouth to said teeth whereby said body may extend along inner sides of said teeth to block contact between said tongue and at least some of said teeth and means formed in at least one of said plates for receiving a vacuum tube in communication with said suction passage.

2. The ejector of claim 1 wherein said passage extends to said upper portion of said body, and wherein said upper portion of said body is formed with at least one suction relief aperture in communication with said passage.

3. The ejector of claim 1 wherein said passage extends continuously along edges of said body from said lower portion to said upper portion of said body, said body being formed with an aperture extending through said upper portion into said passage to provide a relief port.

4. The ejector of claim 1 wherein said body has two major dimensions and a minor dimension and is flattened along the direction of said minor dimension, said first and second plates being in face to face contiguity along a surface bisecting said body and transverse to said minor dimension, said plates having mating recesses that collectively define said suction passage.

5. The ejector of claim 4 including flexible hinge means interconnecting said plates for movement between an open position in which said plates are mutually spaced and a closed position in which said plates are in said face to face contiguity.

6. A saliva ejector comprising, first and second mutually mating body sections each having a recess formed therein, a plurality of apertures extending through at least one of said sections into said recesses, and a groove in each body section communicating with the respeptive recesses, means for securing said mating sections to each other with the recess and groove of one section mating with the recess and groove of the other section, said mating recesses collectively defining a suction passage and said mating grooves collectively defining a vacuum tube receiving bore adapted to receive a vacuum tube.

7. The ejector of claim 6 wherein each section is formed of a flat plate having said recesses extending adjacent and along edges of said plates.

8. The ejector of claim 6 wherein said recesses and said passage extend along and between mutually opposite edges of said body sections.

9. The ejector of claim 6 including means for connecting said sections to each other for motion from an open side by side position wherein said recesses and grooves of one section are spaced from each other to a closed position wherein said recesses and grooves define said passage and bore.

10. The ejector of claim 9 wherein said means for connecting said sections comprises a hinge.

11. The ejector of claim 9 wherein said means for connecting said sections comprises a flexible hinge member fixed to both said sections.

12. The ejector of claim 9 wherein said sections are integral with each other.

13. The ejector of claim 12 wherein said means for connecting said sections comprises a flexible hinge member integral with both said sections.

14. The ejector of claim 6 wherein said means for securing said sections comprises resilient latch means having mating parts integral with respective ones of said sections.

15. The ejector of claim 6 wherein said recesses extend to upper and lower portions of said body sections, some of said apertures extending into said recesses at lower body portions to provide suction and at least one of said apertures extending into said recesses at upper body portions to provide a relief port.

16. The ejector of claim 6 wherein said vacuum tube receiving bore extends upwardly of said body at one end thereof.

17. The ejector of claim 16 including means connecting said sections to each other for relative pivotal movement about a line parallel to the extent of said vacuum tube receiving bore.

18. The ejector of claim 16 including means connecting said sections of each other for relative pivotal movement about a line parallel to the extent of part of said suction passage.

19. The ejector of claim 6 wherein said bore extends along an upper edge of said body whereby said ejector will depend from a vacuum tube received in said bore.

20. A saliva ejector comprising, first and second congruent plates each having an inner and outer side, at least one of said plates having a recess formed therein opening to said inner side thereof, said recess having a closed end and an open end, at least one of said plates being formed with a plurality of apertures extending into said recess, and means for connecting said congruent plates to each other with said inner sides in face to face contiguity, said recess and the other of said plates collectively defining a passage having a closed end said open end adapted to be connected to a vacuum tube and an open end.

21. The ejector of claim 20 wherein said recess and said passage extend continuously along edges of said plates from upper to lower portions of said plates, different ones of said apertures extending into said recess and passage at upper and lower portions of said plates.

22. The ejector of claim 20 including means for hingedly interconnecting said plates.

23. The ejector of claim 22 wherein said plates and said means for interconnecting are all integral with each other.

24. The ejector of claim 20 wherein said recess and passage define a relatively enlarged cylindrical opening at said open end adapted to receive a vacuum tube.

25. The ejector of claim 24 including a vacuum tube adapted to be connected to a source of low pressure, said tube having an end portion received and clamped in said enlarged cylindrical opening.

26. The ejector of claim 25 including
a clamp having first and second opposed parts mutually spaced from each other at one end of each to define a clamp opening receiving said vacuum tube, and means for mutually interconnecting said parts at the other end of each and for urging said parts toward each other at said one end of each,
an elongated tongue mounted on and extending from said first clamp part,
a first handle extending from said first clamp part, and
a second handle extending from said second clamp part in spaced juxtaposition to said first handle, whereby said handles may be moved toward each other to move said clamp parts away from each other to increase the size of said clamp opening for attachment and detachment of said chin holder to and from said vacuum tube.

27. A chin holder adapted to be positioned upon a vacuum tube comprising,
a clamp having first and second opposed parts mutually spaced from each other at one end of each to define a clamp opening adapted to receive said vacuum tube, and means for mutually interconnecting said parts at the other end of each and for urging said parts toward each other at one end of each,
an elongated tongue mounted on and extending from said first clamp part,
a first handle extending from said first clamp part, and
a second handle extending from said second clamp part in spaced juxtaposition to said first handle, whereby said handles may be moved toward each other to move said clamp parts away from each other to increase the size of said clamp opening for attachment and detachment of said chin holder to and from said vacuum tube.

28. The chin holder of claim 27 wherein said first and second parts are integral with other to form a substantially C-shaped integral body having a partly circular opening defining said clamp opening, said means for interconnecting and urging said parts comprising a portion of said integral body between said first and second parts.

29. The instrument of claim 28 wherein at least one of said handles is integral with said body.

30. The instrument of claim 28 wherein said tongue and both said handles are integral with said body.

31. A chin holder for a dental appliance comprising,
an elongated tongue adapted to firmly contact a person beneath the chin, and
a side opening clamp integral with said tongue, said clamp comprising,
a substantially C-shaped body having first and second mutually spaced side legs, at least one of said legs being formed of a resilient material to permit said side legs to be moved away from each other and to urge said side legs toward each other from a displaced position thereof,
a first handle on said first leg, and a second handle on said second leg in spaced juxtaposition to said first handle, whereby said handles may be moved relative to each other to move said side legs away from each other and permit said side opening clamp to be attached to, adjusted along, and removed from a vacuum tube of a dental appliance without disturbing the appliance or tube.

32. The chin holder of claim 31 wherein one of said handles is connected to one of said side legs and extends along and in spaced relation to at least one of said legs.

33. The chin holder of claim 31 wherein said tongue extends in one direction laterally of said clamp body and said handles extend in a second direction laterally of said clamp body and at an angle to said first direction.

34. The chin holder of claim 31 wherein said handles are integral with said clamp body and extend in substantially the same direction from one side of said clamp body, and wherein said tongue extends in an opposite direction from the other side of said clamp body.

35. The chin holder of claim 31 wherein one of said handles is connected to and extends outwardly from an end of one of said side legs, and wherein the other of said handles is connected to the other of said side legs and extends along said intermediate leg toward said one side leg.

* * * * *

UNITED STATES PATENT AND TRADEMARK OFFICE
CERTIFICATE OF CORRECTION

PATENT NO. : 4,017,975
DATED : April 19, 1977
INVENTOR(S) : Wesley Grant Johnson It is certified that error appears in the above-identified patent and that said Letters Patent are hereby corrected as shown below:

Col. 2, line 16:  correct spelling of "justaposition" to ---juxtaposition---;

Col. 5, line 54:  insert a parenthesis after "molded";

Col. 6, line 7:  change "well," to ---wells---;

Col. 8, line 32:  after "vacuum tube" insert a period and delete "and an open end".

Signed and Sealed this twenty-sixth Day of July 1977

[SEAL]

Attest:

RUTH C. MASON
*Attesting Officer*

C. MARSHALL DANN
*Commissioner of Patents and Trademarks*